United States Patent
Yang et al.

(10) Patent No.: US 11,510,933 B2
(45) Date of Patent: Nov. 29, 2022

(54) **USE OF *PULSATILLA CHINENSIS* EXTRACT IN THE PREPARATION OF DRUGS FOR TREATMENT OF VIRAL AND/OR BACTERIAL DISEASES**

(71) Applicant: SICHUAN INLU WEITE PHARMACEUTICAL TECHNOLOGY CO., LTD., Sichuan (CN)

(72) Inventors: Shilin Yang, Sichuan (CN); Zhetong Su, Sichuan (CN)

(73) Assignee: SICHUAN INLU WEITE PHARMACEUTICAL TECHNOLOGY CO., LTD., Sichuan (CN)

( * ) Notice: Subject to any disclaimer, the term of this patent is extended or adjusted under 35 U.S.C. 154(b) by 58 days.

(21) Appl. No.: 16/966,857

(22) PCT Filed: Jan. 25, 2019

(86) PCT No.: PCT/CN2019/073238
§ 371 (c)(1),
(2) Date: Jul. 31, 2020

(87) PCT Pub. No.: WO2019/149155
PCT Pub. Date: Aug. 8, 2019

(65) Prior Publication Data
US 2021/0038623 A1 Feb. 11, 2021

(30) Foreign Application Priority Data
Jan. 31, 2018 (CN) .......................... 201810097221.3

(51) Int. Cl.
| A61K 31/704 | (2006.01) |
| A61P 31/12 | (2006.01) |
| A61P 31/04 | (2006.01) |
| A61P 31/00 | (2006.01) |
| A61K 9/00 | (2006.01) |

(52) U.S. Cl.
CPC .......... *A61K 31/704* (2013.01); *A61K 9/0019* (2013.01); *A61P 31/00* (2018.01); *A61P 31/04* (2018.01); *A61P 31/12* (2018.01)

(58) Field of Classification Search
CPC .......... A61K 31/704; A61P 31/04; A61P 31/12
See application file for complete search history.

(56) References Cited

U.S. PATENT DOCUMENTS

2021/0038622 A1* 2/2021 Yang .................. A61P 31/00

FOREIGN PATENT DOCUMENTS

| CN | 101337033 A | 1/2009 |
| CN | 101732517 A | 6/2010 |
| CN | 102100753 A | 6/2011 |
| CN | 104083564 A | 10/2014 |
| CN | 105213410 A | 1/2016 |
| CN | 105535004 A | 5/2016 |
| KR | 20160019772 A | 2/2016 |

OTHER PUBLICATIONS

English machine translation of CN105535004A, downloaded from https://worldwide.espacenet.com (Year: 2016).*
Zhao et al., "Pulsatilla chinensis: A review of traditional uses, phytochemistry and pharmacology research progress" Arabian Journal of Chemistry vol. 14 pp. 1-15 https://doi.org/10.1016/j.arabjc.2021.103403 (Year: 2021).*
English machine translation of CN 102100753, obtained from worldwide.espacenet.com (Year: 2011).*
English machine translation of CN 104083564, obtained from worldwide.espacenet.com (Year: 2014).*
English machine translation of CN 101337033, obtained from worldwide.espacenet.com (Year: 2007).*
English machine translation of CN 101732517, obtained from worldwide.espacenet.com (Year: 2009).*
Yang et al., "Antiviral and immunoregulatory role against PCV2 in vivo of Chinese herbal medicinal ingredients" J Vet Research vol. 61 pp. 405-410 DOI:10.1515/jvetres-2017-0062 (Year: 2017).*

(Continued)

*Primary Examiner* — Eric Olson
(74) *Attorney, Agent, or Firm* — Novick, Kim & Lee, PLLC; Allen Xue (57) ABSTRACT

Disclosed are uses of a *Pulsatilla* saponin compound B4 or a pharmaceutically acceptable salt thereof in preparing a drug for treating viral and/or bacterial diseases. The *Pulsatilla* saponin compound B4 disclosed by the invention shows a strong biological activity, and efficiently treats endometritis, footrot, feline parvovirus, canine parvovirus, canine distemper, canine kidney failure, and canine acute nephritis.

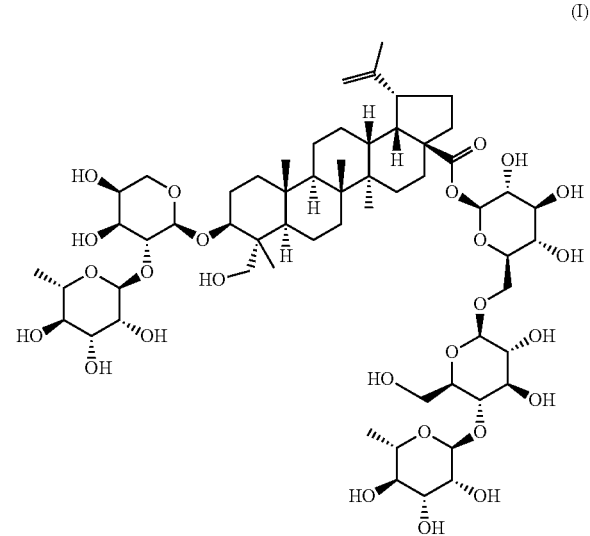

5 Claims, 1 Drawing Sheet (56) References Cited

OTHER PUBLICATIONS

Tang et al., "Traditional Chinese medicine" The Lancet vol. 372 pp. 1938-1940 DOI:10.1016/S0140-6736(08)61354-9 (Year: 2008).*

Hu, Yiyi et al.; Effects of Pulsatillae Decoction and its Ingredients on Endothelial Cell to Secrete TNF-a, TXB2 and 6-keto-PGF1a; Journal of Jilin Agricultural University; vol. 36, No. 3, Jun. 15, 2014; ISSN: 1000-5684.

Hu, Yiyi et al.; Effects of Pulsatillae Decoction and Its Ingredients on Lipopolysaccharide-induced Endothelial Cell to Secrete IL-1a,IL-6 and ET-1 in Vetro; Journal of Nanjing Agricultural University; vol. 37, No. 2, Mar. 30, 2014, pp. 116-120.

Hu, Yiyi et al.; Effects of Pulsatillae Decoction and its Ingredients on Endothelial Cell to Secrete TNF-a, TXB2 and 6-keto-PGF1a; Journal of Jilin Agricultural University; vol. 36, No. 3, Jun. 15, 2014; ISSN: 1000-5684, pp. 116-120.

Hu, Yiyi et al.; Effects of Pulsatillae Decoction and Its Ingredients on LPS-induced Endothelial Cell to Secrete NO, E-selectin, and IL-8; Chinese Journal of Animal and Veterinary Sciences; vol. 43, No. 1, Jan. 15, 2012. ISSN: 0366-6964. pp. 145-151.

\* cited by examiner

Fig. 1

USE OF PULSATILLA CHINENSIS EXTRACT IN THE PREPARATION OF DRUGS FOR TREATMENT OF VIRAL AND/OR BACTERIAL DISEASES

TECHNICAL FIELD

The present invention relates to the use of *Pulsatilla chinensis* extract in the preparation of drugs for treatment of viral and/or bacterial diseases.

BACKGROUND ART

*Pulsatilla chinensis* (Bge.) Regel belongs to *Pulsatilla* genus of Ranunculaceae family, whose main medicinal part is its dry root. The earliest record of *Pulsatilla chinensis* is found in Shennong Herbal Classic. *P. chinensis* is bitter in taste and cold in nature, as well as in stomach, kidney and large intestine meridians. Its efficacy mainly includes eliminating redundancy, cooling blood, stopping diarrhea, and reducing internal heat, and it is traditionally used for treatment of bacterial dysentery, as well as has good therapeutic effect on cold, heat, and wen diseases, red and pain of eyes and so on. The pharmacological activities of *Pulsatilla chinensis* are various, and can mainly consist of improving the ability of the body to recognize and resist the invasion of foreign microbes, reducing the proliferative rate of tumor cells, lessening the number of pathogenic microorganisms, and effectively inhibiting the oxidative reaction of free radicals. Among them, the most potential application is in the development of new anti-inflammatory and anti-tumor drugs. Feng Xiuzhi et al. studied the effect of *P. chinensis* on cell apoptosis, and thought that it had a good induction action on gastric cancer cells. In addition, the proliferation and DNA replication of cancer cells are related to the active ingredients of *P. chinensis*, which can inhibit the growth of HL260 cells, and the proliferation of breast cancer (MCF-7), lung cancer (PG), colon cancer (SW480), and malignant glioma cells (U87MG) by inducing apoptosis. Li Wenchao et al. used the ethanolic extract of *P. chinensis* to treat various pathogenic bacteria, and studied the antibacterial effect of different solvent extracts, and found that all of them had antibacterial effect, but the effect was different. At present, there is no report on the use of compounds of the present invention for treatment of viral and/or bacterial diseases according to the present invention.

CONTENT OF THE INVENTION

In order to solve the above technical problems, the present invention provides the use of compound anemoside B4 of formula I or pharmaceutically acceptable salts thereof in the preparation of drugs for treatment of viral and/or bacterial diseases.

I

Further, said pharmaceutical is a preparation obtained by using forementioned compound anemoside B4 or pharmaceutically acceptable salts thereof as active components, with addition of pharmaceutically acceptable excipients.

Further, said preparations are injection, intrauterine injection, pulvis, paste, and lotion.

Further, said preparations are injection, intrauterine injection, and pulvis.

Further, said diseases are endometritis, foot rot disease, parvovirus, canine distemper, canine renal failure, and canine acute nephritis.

Further, said endometritis is clinical endometritis; said parvovirus disease is canine parvovirus disease and feline parvovirus disease.

The present invention also provides a pharmaceutical for treatment of viral and/or bacterial diseases, that is a preparation obtained by using forementioned compound anemoside B4 or pharmaceutically acceptable salts thereof as active components, with addition of pharmaceutically acceptable excipients.

Further, said preparations are injection, intrauterine injection, pulvis, paste, and lotion; preferably, said preparations are injection, intrauterine injection, and pulvis.

Further, said diseases are endometritis, foot rot, parvovirus, canine distemper, canine renal failure, and canine acute nephritis.

Further, said endometritis is clinical endometritis; said parvovirus disease is canine parvovirus disease and feline parvovirus disease.

The extract of *P. chinensis* provided in the present invention is compound anemoside B4, with a CAS number 129741-57-7. It's molecular formula is $C_{59}H_{96}O_{26}$, corresponding to the molecular weight 1221.38, and obtained as white crystalline powder.

Anemoside B4 of the present invention has strong biological activity, as well as excellent therapeutic effects on endometritis, foot rot disease, feline parvovirus, canine parvovirus, canine distemper, canine renal failure, and canine acute nephritis.

Obviously, based on above content of the present invention, according to the common technical knowledge and the conventional means in the field, without department from above basic technical spirits, other various modifications, alternations or changes can further be made.

By following specific examples, above content of the present invention is further illustrated. But it should not be construed that the scope of above subject of the present invention is limited to following examples. The techniques realized based on above content of the present invention are all within the scope of the present invention.

EXAMPLES

Example 1

Preparation of the Compound According to the Present Invention 100 kg *Pulsatilla chinensis* was added 70% ethanol (1/10, V/V), heated under reflux, and extracted 2 times. The extracting solution was concentrated under reduced pressure at 75° C., and then centrifuged at 4000 r/min for 10 min. The supernatant was passed through polar macroporous adsorption resin column, successively eluting with water, 30% ethanol and 70% ethanol. The part eluted with 70% ethanol was concentrated at 75° C. under reduced pressure, then spray-dried to obtain the total saponin extract of *P. chinensis* (3450 g). The resultant extract was dissolved in water and filtered. The filtrate was subjected to Dynamic axial preparative chromatographic system (packed with 10 μm ODS) and eluted with 50% methanol. The corresponding eluent was collected according to the chromatographic peaks. After concentrated under reduced pressure, anemoside B4 (1700 g) was obtained followed by freeze-drying.

Example 2

Content Determination of the Compound According to the Present Invention

1. Apparatus and Tested Drugs

Agilent 1260 HPLC apparatus and DAD UV detector were purchased from Agilent Technology (China) Co., Ltd. BP211D electronic analytical balance was purchased from Sartorius Company (Germany). KQ-400DB numerical control ultrasonic cleaner was purchased from Kunshan Ultrasonic Instrument Co., Ltd.

Sample of anemoside B4, prepared in example 1.

Reference substance of anemoside B4 (Lot No. 111766-201702; content: 94.7%), purchased from National Institutes for Food and Drug Control.

2. Chromatographic Conditions

Chromatographic column: Sepax Bio-C18 (4.6×250 mm, 5 μm); mobile phase: MeOH—H$_2$O (64:36); detection wavelength 201 nm; flow rate 1.0 ml/min.

3. Preparation of Reference Solution

Reference substance of anemoside B4 was accurately weighed and put into a 10 mL volumetric flask, to which was added mobile phase to dissolve, and then the mobile phase was added to the scale, to obtain the reference solution (1 mg anemoside B4/1 mL).

4. Preparation of Sample Solution

Anemoside B4 (10 mg) prepared in example 1 was accurately weighed and put into a 10 mL volumetric flask, to which was added mobile phase to dissolve, and then the mobile phase was added to the scale, to obtain the sample solution.

5. Determination Method

20 μL of reference solution and sample solution was accurately measured, respectively, and injected into liquid chromatograph, to record the chromatogram and calculate the content according to external standard method.

6. Standard Curve and Linear Regression Equation

Figure 1:
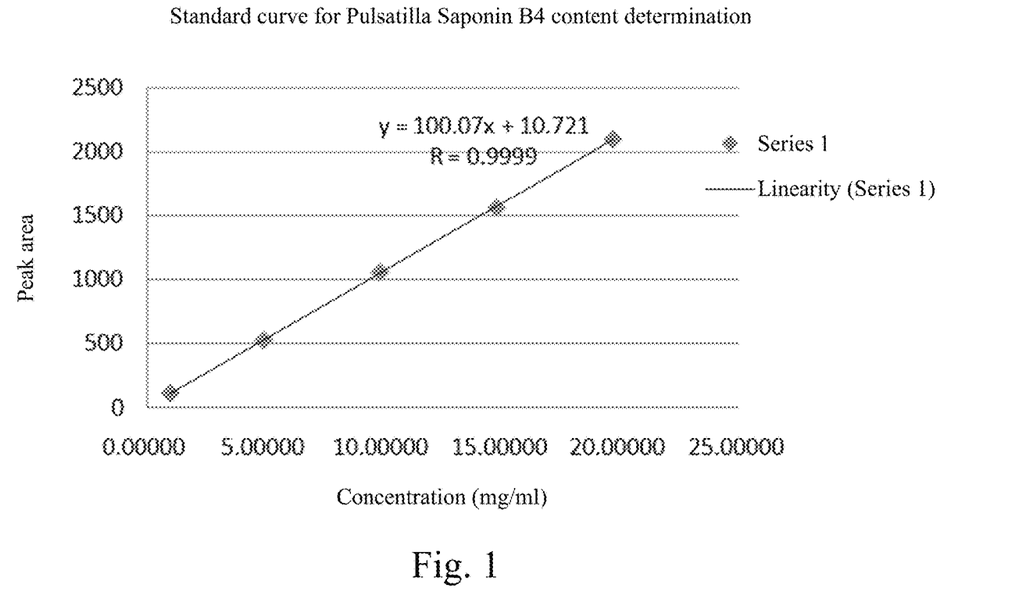
FIG. 1 shows the standard curve for the content determination of anemoside B4.

Reference substance of anemoside B4 was accurately weighed and put into a 10 mL volumetric flask, to which was added mobile phase to dissolve, and then the mobile phase was added to the scale, to obtain the reference solutions at concentrations of 1 mg/mL, 5 mg/mL, 10 mg/mL, 15 mg/mL, and 20 mg/mL. 20 μL of each solution was accurately measured and injected into the liquid chromatograph, to record the chromatogram.

TABLE 1

Linear regression equation for content determination of anemoside B4

| Sample | Concentration (mg/mL) | Peak area | Regression equation |
|---|---|---|---|
| 1 | 0.98488 | 115.7 | Y = 100.07 + 10.721 |
| 2 | 4.92440 | 529.5 | R = 0.9999 |
| 3 | 9.84880 | 1057.8 | |
| 4 | 14.77320 | 1560.3 | |
| 5 | 19.69760 | 2097.9 | |

According to the results, the linear relationship of anemoside B4 was good in the concentration range of 1.0~20.80 mg/mL (r=0.9999), which was suitable for the content determination of anemoside B4.

7. The Content Determination for Sample of Anemoside B4

According to the method described in "3" above, two parts of reference substances of anemoside B4, 10 mg each, were accurately weighed and put into 10 mL volumetric flasks, respectively, to which was added mobile phase to dissolve, and then the mobile phase was added to the scale, to obtain the reference solution 1 and the reference solution 2.

According to the method described in "4" above, two parts of samples of anemoside B4, 10 mg each, were accurately weighed and put into 10 mL volumetric flasks, respectively, to which was added mobile phase to dissolve, and then the mobile phase was added to the scale, to obtain the sample solution 1 and the sample solution 2.

According to above chromatographic conditions, 20 μL of each solution was precisely measured and injected into the liquid chromatograph, to record the chromatogram.

TABLE 2

Determination results for the content of sample of anemoside B4

| Sample | Amount (mg) | Peak area | Concentration (mg/mL) | Content (%) | Average content (%) |
|---|---|---|---|---|---|
| Reference solution 1 | 10.22 | 1039.6 1044.4 | 0.968 | // | // |
| Reference solution 2 | 10.05 | 1025.6 1022.5 | 0.952 | // | // |
| Sample solution 1 | 10.13 | 1081.8 1092.6 | 1.013 | 99.7 | 99.4 |
| Sample solution 2 | 10.10 | 1075.1 1079.2 | 1.010 | 99.1 | |

According to the experimental results, the content of anemoside B4 obtained in this experiment was 99.4%.

Example 3

Preparation of Anemoside B4 Injection According to the Present Invention

1) Formula: 1000 mL injection was prepared by adding water to 50 g anemoside B4.
2) Preparative method: 50 g anemoside B4 prepared in example 1 was weighed and added 800 mL water for injection to dissolve it completely. The solution was filtered and adjusted to pH 7.0, to which was then added injectable water to 1000 mL. The resultant solution was finely filtered, filled, sealed, and sterilized at 100° C. for 30 min, to obtain the injection.

Example 4

Preparation of Anemoside B4 Pulvis According to the Present Invention

1) Formula: 1000 g anemoside B4 was prepared as 1000 g pulvis.
2) Preparative method: 1000 g anemoside B4 prepared in example 1 was weighed, crushed into fine powder, passed through 100 mesh sieve, and mixed well, to obtain the pulvis.

Example 5

Preparation of Anemoside B4 Intrauterine Injection According to the Present Invention 1) Formula: 50 g anemoside B4 was prepared as 1000 mL intrauterine injection.
2) Preparative method: 50 g anemoside B4 prepared in example 1 was weighed and added with distilled water (800 mL) to dissolve it completely. The solution was filtered and adjusted to pH 7.0, to which was then added distilled water to 1000 mL. The resultant solution was finely filtered, filled, sealed, and sterilized at 100° C. for 30 min, to obtain the intrauterine injection.

The beneficial effect of the present invention was illustrated by means of experimental examples.

Experimental Example 1

Experiment on Endometritis

1. Test Drugs

Anemoside B4 injection prepared in example 3, with a concentration of 50 mg/mL; Anemoside B4 intrauterine injection prepared in example 5, with a concentration of 50 mg/mL.

Positive drug: doxycycline hydrochloride intrauterine injection (24 g/injection, produced by Zhengzhou Bairui Animal Pharmaceutical Co., Ltd., batch No.: 170901).

2. Test Animals 130 cows with disease were randomly divided into 13 groups, 10 cows for each group.

The cows selected in this experiment were all those with clinical endometritis. During the experiment, the temperature, spirit and diet of the cows were normal.

3. Dosage and Mode of Administration

TABLE 3

Dosage and mode of administration

| Groups | Administration dosage (mL/time) | Administration mode |
|---|---|---|
| Blank control group | Physiological saline | / |
| Positive drug group | 1 | Intrauterine infusion |
| Low-dose group for intramuscular injection of anemoside B4 | 10 | intramolecular injection |
| Medium-dose group for intramuscular injection of anemoside B4 | 20 | intramolecular injection |
| High-dose group for intramuscular injection of anemoside B4 | 30 | intramolecular injection |
| Low-dose group for intravenous injection of anemoside B4 | 20 | intravenous injection |
| Medium-dose group for intravenous injection of anemoside B4 | 40 | intravenous injection |
| High-dose group for intravenous injection of anemoside B4 | 60 | intravenous injection |
| Low-dose group for intrauterine injection of anemoside B4 | 10 | intrauterine injection |
| Medium-dose group for intrauterine injection of anemoside B4 | 20 | intrauterine injection |
| High-dose group for intrauterine injection of anemoside B4 | 30 | intrauterine injection |

Administration by intramolecular injection: Administrating anemoside B4 by intramulscular injection, twice per day, one in the morning and another in the evening, for successive four days;

Administration by intrauterine infusion: administrating anemoside B4 and positive drug doxycycline hydrochloride by intrauterine infusion, once every other day, for 4 times.

A blank control group was set up in different administration routes, and the same dose of normal saline was administered.

4. The Criteria for Diagnosis and Therapeutic Effect of Endometritis

TABLE 4

The criteria for diagnosis and therapeutic effect of endometritis

| Type of endometritis | Diagnostic criteria | Criteria for judging therapeutic effect |
|---|---|---|
| Clinical endometritis | Frequently occurring 7-25 days after childbirth, with loss of appetite, decreasing in milk production, temperature rising, mental depression, roachback, tail-lifting, abdomen-contracting, often having urination posture; mucinous or purulent exudate discharging through the vulva, sometimes mixed with blood; when lying down, more exudate discharging, accompanied by fishy smell. Through rectal palpation, the cervix was not completely closed, and the size of the uterus failed to return to normal. | After 3 courses of treatment, the secretion of the uterus was clear or slightly white, without pus and obvious clinical symptoms, and the uterus returned to normal contractive response. The successful mating within 3 estrous periods after delivery was effective; After 3 courses of treatment, flocculent fragments or pus were still mixed in the excreta of uterus, and the clinical symptoms did not disappear. Incomplete palpation contraction of uterus or thick and hard uterine horn were uneffective. |
| subclinical endometritis | The vaginal and cervical mucosa of cows were congested and swollen, secretion was discharged, and | After 3 courses of treatment, the uterine contraction was normal, the secretion was clear or slightly white, |

TABLE 4-continued

The criteria for diagnosis and therapeutic effect of endometritis

| Type of endometritis | Diagnostic criteria | Criteria for judging therapeutic effect |
|---|---|---|
| | odor was emitted. Direct examination showed that the cervix mouth was incomplete, damaged and proliferated, the uterine wall was thickened, the morphology of uterine horn was changed, and the uterine body was drooping. The palpation lead to pain. | without abscess, and the clinical symptoms of sick cows disappeared, and the pregnancy was effective in three estrous periods; After 3 courses of treatment, flocculent debris or abscess were mixed in the excreta of uterus. The clinical symptoms did not disappear, and the incomplete uterine contraction by palpation was invalid. |

5. Experimental Results

The experimental results of anemoside B4 for treatment of cow clinical endometritis are shown in Table 5

TABLE 5

The experimental results of anemoside B4 for treatment of cow clinical endometritis by intramulscular injection ($\bar{x} \pm SD$, n = 10)

| Groups | Parity | Mean time of first estrus after medication (day) | Oestrus rate (%) | Pregnancy rate in three estrous periods after delivery (%) |
|---|---|---|---|---|
| Blank control group | 2.2 ± 0.5 | 22 ± 5.1 | 35 | 31 |
| Positive drug group | 2.6 ± 0.6 | 26 ± 6.6 | 58* | 50* |
| Low-dose group for intramulscular injection of anemoside B4 injection | 2.4 ± 0.8 | 27 ± 5.8 | 54 | 42 |
| Medium-dose group for intramulscular injection of anemoside B4 injection | 2.6 ± 0.4 | 26 ± 4.6 | 60 | 52 |
| High-dose group for intramulscular injection of anemoside B4 injection | 2.7 ± 0.6 | 25 ± 5.5 | 65* | 56* |

Note:
*denotes the obvious difference compared with the blank control group, $p < 0.05$.

TABLE 6

The experimental results of anemoside B4 injection for treatment of cow clinical endometritis by intravenus injection ($\bar{x} \pm SD$, n = 10)

| Groups | Parity | Mean time of first estrus after medication (day) | Oestrus rate (%) | Pregnancy rate in three estrous periods after delivery (%) |
|---|---|---|---|---|
| Blank control group | 2.2 ± 0.5 | 22 ± 5.1 | 35 | 31 |
| Positive drug group | 2.6 ± 0.6 | 26 ± 6.6 | 58* | 50* |
| Low-dose group for intravenous injection of anemoside B4 | 2.5 ± 0.5 | 27 ± 6.4 | 57 | 46 |
| Medium-dose group for intravenous injection of anemoside B4 | 2.6 ± 0.7 | 26 ± 4.3 | 63 | 52 |
| High-dose group for intravenous injection of anemoside B4 | 2.7 ± 0.4 | 24 ± 5.2 | 68* | 58* |

Note:
*denotes the obvious difference compared with the blank control group, $p < 0.05$.

TABLE 7

The experimental results of anemoside B4 for treatment of cow clinical endometritis by intrauterine infusion ($\bar{x} \pm SD$, n = 10)

| Groups | Parity | Mean time of first estrus after medication (day) | Oestrus rate (%) | Pregnancy rate in three estrous periods after delivery (%) |
|---|---|---|---|---|
| blank control group | 2.2 ± 0.5 | 22 ± 5.1 | 35 | 31 |
| positive drug group | 2.6 ± 0.6 | 26 ± 6.6 | 58* | 50* |
| Low-dose group for intrauterine infusion of anemoside B4 | 2.5 ± 0.8 | 25 ± 5.4 | 64 | 52 |
| Medium-dose group for intrauterine infusion of anemoside B4 | 2.7 ± 0.5 | 24 ± 7.3 | 74* | 70* |
| High-dose group for intrauterine infusion of anemoside B4 | 2.9 ± 0.3 | 23 ± 6.2 | 78* | 75* |

Note:
*denotes the obvious difference compared with the blank control group, $p < 0.05$.
According to the experimental results, after administration, in the high-dose group for intramulscular injection of anemoside B4 injection, the high-dose group for intravenus injection of anemoside B4 injection, the medium-dose group for intrauterine infusion of anemoside B4, and the high-dose group for intrauterine infusion of anemoside B4, as well as the positive drug group, the estrus rate of cows and the conception rate in three estrous periods after delivery were significantly higher than that of the blank control group, indicating that anemoside B4 has a significant effect in the treatment of clinical endometritis, and it is superior to the doxycycline hydrochloride uterine injection.

Experimental Example 2

Experiment on Foot Rot Disease

1. Test Drugs

Anemoside B4 injection prepared in example 3, with a concentration of 50 mg/mL; Anemoside B4 pulvis prepared in example 4, with a content of 99.4%.

Positive drug: Penicillin powder (North China Pharmaceutical Co., Ltd.).

2. Test Animals 130 cows with foot rot disease were randomly divided into 13 groups, 10 cows for each group.

3. Dosage and Mode of Administration

TABLE 8

Table 3 Dosage and mode of administration
Dosage and mode of administration

| Groups | Dose of administration | Mode of administration |
|---|---|---|
| Blank control group | Physiological saline | / |
| Positive drug group | $1.60 \times 10^6$ units | External application |
| Low-dose group for subcutaneous injection of anemoside B4 injection | 5 mL | Subcutaneous injection |
| Medium-dose group for subcutaneous injection of anemoside B4 injection | 10 mL | Subcutaneous injection |
| High-dose group for subcutaneous injection of anemoside B4 injection | 15 mL | Subcutaneous injection |
| Low-dose group for intravenus injection of anemoside B4 injection | 20 mL | intravenus injection |
| Medium-dose group for intravenus injection of anemoside B4 injection | 40 mL | intravenus injection |
| High-dose group for intravenus injection of anemoside B4 injection | 60 mL | intravenus injection |
| Low-dose group for anemoside B4 pulvis | 0.5 g | External application |
| Medium-dose group for anemoside B4 pulvis | 1.0 g | External application |
| High-dose group for anemoside B4 pulvis | 1.5 g | External application |

Administration by subcutaneous injection: anemoside B4 injection was administered subcutaneously in the affected limbs once a day for 4 days.

Administration by intravenus injection: anemoside B4 injection was administered by intravenous injection once a day for 4 days.

Administration by external application: anemoside B4 pulvis and the positive drug penicillin powder were administered by bandaging, once every other day, for a total of 4 times. The wound was rinsed with 5% $KMnO_4$ solution, and the necrotic tissue was removed until blood oozed out. The powder was applied on the wound, and then wrapped with 8-10 layers of sterile gauze.

A blank control group was set up in different administration ways, and the same dose of normal saline was administered.

4. Symptoms and Treatment Evaluation Criteria of Cows with Foot Rot Disease 4.1 Symptoms of Cows with Foot Rot Disease Cows with hoof rot disease prefer to lie down, stand up for a short time, are unwilling to fully land their hoofs, feel pain in the affected limbs, and limp; in an acute attack, the crown of the hoof and the surface between toes became irritated, swollen, sensitive, warm, and painful when tapping or pressing the affected area. Afterwards, the wound can be seen. After the wound is enlarged, black decaying liquid flows out, and an ulcer surface is formed between the toes, which is covered with foul-smelling necrosis. The affected cow loses appetite, gradually loses weight, has coarse back hair, and reduces milk production.

4.2 Treatment Evaluation Criteria

Complete cure: the spirit, diet, and body temperature of the affected cow return to normal; the clinical symptoms in the affected area disappear completely, and lactation becomes normal. Clinical cure: the spirit, diet, and body temperature of the affected cow return to normal; the clinical symptoms in the affected area basically disappear, and lactation basically become normal. Invalid: The clinical symptoms in the affected area are not significantly improved or even worsened, or they recur within two weeks of stopping the drug, and both are considered uneffective. The total number of cured cows is the sum of the number of completely cured cows and the number of clinically cured cows.

5. Experimental Results

TABLE 9

The experimental results of anemoside B4 injection for treatment of cow foot rot disease by subcutaneous injection ($\bar{x} \pm SD$, n = 10)

| Groups | Total number of cured cows | Milk production (daily yield) kg/cow |
|---|---|---|
| Blank control group | 1 | 14.8 ± 2.2 |
| Positive drug group | 7 | 21.2 ± 1.3 |
| Low-dose group for subcutaneous injection of anemoside B4 injection | 5 | 20.4 ± 1.9 |
| Medium-dose group for subcutaneous injection of anemoside B4 injection | 7 | 22.1 ± 1.6 |
| High-dose group for subcutaneous injection of anemoside B4 injection | 8 | 25.6 ± 2.8* |

Note:
*denotes the obvious difference compared with the blank control group, $p < 0.05$.

TABLE 10

The experimental results of anemoside B4 injection for treatment of cow foot rot disease by intravenus injection ($\bar{x} \pm SD$, n = 10)

| Group | Total number of cured cows | Milk production (daily yield) kg/cow |
|---|---|---|
| Blank control group | 1 | 14.8 ± 2.2 |
| Positive drug group | 7 | 21.2 ± 1.3 |
| Low-dose group for intravenus injection of anemoside B4 injection | 4 | 18.2 ± 1.4 |
| Medium-dose group for intravenus injection of anemoside B4 injection | 5 | 20.8 ± 2.2 |
| High-dose group for intravenus injection of anemoside B4 injection | 6 | 22.2 ± 1.5 |

Note:
*denotes the obvious difference compared with the blank control group, $p < 0.05$.

TABLE 11

The experimental results of anemoside B4 pulvis for treatment of cow foot rot disease ($\bar{x} \pm SD$, n = 10)

| Groups | Total number of cured cows | Milk production (daily yield) kg/cow |
|---|---|---|
| Blank control group | 1 | 14.8 ± 2.2 |
| Positive drug group | 7 | 21.2 ± 1.3 |
| Low-dose group for anemoside B4 pulvis | 6 | 22.6 ± 2.5 |
| Medium-dose group for anemoside B4 pulvis | 8 | 24.2 ± 1.7* |
| High-dose group for anemoside B4 pulvis | 9 | 25.9 ± 2.4* |

Note:
*denotes the obvious difference compared with the blank control group, $p < 0.05$.

According to the experimental results, when anemoside B4 was used for treatment of foot rot disease in dairy cows, their mental, diet and body temperature in each treatment group were greatly improved, and milk production also increased. Among them, the high-dose group for anemoside B4 injection by subcutaneous injection, the middle-dose group of anemoside B4 pulvis, and the high-dose group of anemoside B4 pulvis had significantly higher milk production than the blank control group, and the effect was better than that of the positive drug group. The cure rate was above 80%.

Experimental Example 3

Experiment on Canine Parvovirus

1. Test Drug

Anemoside B4 injection prepared in example 3, with a concentration of 50 mg/mL.

2. Test Animals

Dogs suffering from canine parvovirus are cases received by various pet hospitals in Chengdu.

3. Symptoms of Dogs Suffering From Canine Parvovirus

In the early, dogs have high temperature and vomit violently. The vomit changes from white to yellow, and finally to green, with a small amount of blood streak; eyes' conjunctival congestion and tears; liking drinking water and vomiting after drinking; fecal jets are like tomato sauce, smelly and unpleasant; preferring to lie down; the number of white blood cells dropped sharply, together with severe dehydration, heart failure, and shock to death.

4. Dosage and Mode of Administration

Anemoside B4 injection was intravenously injected, 2 mL/time in low-dose group, 4 mL/time in medium-dose group, 8 mL/time in high-dose group, once a day; anemoside B4 injection was intramuscularly injected, 1 mL/time in low-dose group, 2 mL/time in the middle-dose group, 4 mL/time in the high-dose group, twice a day; the treatment was kept for 14 days.

5. Experimental Results

TABLE 12

The research results of anemoside B4 for treatment of canine parvovirus ($\bar{x} \pm SD$, n = 10)

| Groups | Numbers treated (dog) | Body temperature (° C.) | White blood cell count (×10$^9$) | Mortality rate (%) |
|---|---|---|---|---|
| Blank control group | 10 | 39.5 ± 0.4 | 2.1 ± 0.2 | 90 |
| Low-dose group of intramuscular injection | 10 | 39.2 ± 0.5 | 3.3 ± 0.3 | 80 |
| Medium-dose group of intramuscular injection | 10 | 38.4 ± 0.3 | 4.6 ± 0.8 | 60 |
| High-dose group of intramuscular injection | 10 | 37.8 ± 0.4* | 6.2 ± 0.5* | 50 |
| Low-dose group of intravenus injection | 10 | 38.2 ± 0.5* | 6.3 ± 0.4* | 50 |
| Medium-dose group of intravenus injection | 10 | 37.6 ± 0.3* | 7.6 ±0.6* | 40 |
| High-dose group of intravenus injection | 10 | 37.4 ± 0.2* | 8.2 ± 0.7* | 30 |

Note:
*denotes the obvious difference compared with the blank control group, $p < 0.05$.
According to the experimental results, anemoside B4 showed a certain therapeutic effect on canine parvovirus. As the increase of the therapeutic dose, the mortality rate of ill dogs presents a decreasing trend.

Experimental Example 4

Experiment on Feline Parvovirus

1. Test Drug

Anemoside B4 injection prepared in example 3, with a concentration of 50 mg/mL.

2. Test Animals

Cats suffering from feline parvovirus are cases received by various pet hospitals in Chengdu.

3. Symptoms of Cats Suffering From Feline Parvovirus

Cats occasionally having fever, severe vomiting, and diarrhea; the stool changing from gray to yellow and finally to milky white, accompanied by jelly-like mucus; stools liking tomato sauce, smelly and unpleasant; having a lying prone; the number of white blood cells dropping sharply, cold limbs, highly depressed spirit, then shock to death.

4. Dosage and Mode of Administration

Anemoside B4 injection was intravenously injected, 2 mL/time in low-dose group, 4 mL/time in medium-dose group, 8 mL/time in high-dose group, once a day; anemoside B4 injection was intramuscularly injected, 1 mL/time in low-dose group, 2 mL/time in the middle-dose group, 4 mL/time in the high-dose group, twice a day; the treatment was kept for 14 days.

5. Experimental Results

TABLE 13

The research results of anemoside B4 for treatment of feline parvovirus ($\bar{x} \pm SD$, n = 10)

| Groups | Numbers treated (cat) | White blood cell count (×10$^9$) | Mortality rate (%) |
|---|---|---|---|
| Blank control group | 10 | 2.5 ± 0.4 | 90 |
| Low-dose group of intramuscular injection | 10 | 4.7 ± 0.3 | 90 |
| Medium-dose group of intramuscular injection | 10 | 7.8 ± 0.6* | 70 |
| High-dose group of intramuscular injection | 10 | 9.1 ± 0.5* | 50 |
| Low-dose group of intravenus injection | 10 | 7.7 ± 0.4* | 80 |
| Medium-dose group of intravenus injection | 10 | 8.8 ± 0.7* | 60 |
| High-dose group of intravenus injection | 10 | 9.3 ± 0.9* | 40 |

Note:
*denotes the obvious difference compared with the blank control group, $p < 0.05$.
According to the experimental results, anemoside B4 showed a certain therapeutic effect on feline parvovirus, and can significantly reduce the mortality of sick cats and improve the survival rate of sick cats.

Experimental Example 5

Experiment on Treatment of Canine Distemper

1. Test Drug

Anemoside B4 injection prepared in example 3, with a concentration of 50 mg/mL.

2. Test Animals

Dogs suffering from canine distemper are cases received by various pet hospitals in Chengdu.

3. Symptoms of Dogs Suffering From Canine Distemper

According to the clinical symptoms, canine distemper can be divided into early, middle and late stages.

Early stage: the dog is depressed, doesn't like acting and moving, and has a small amount of serous nasal fluid and serous ocular secretions; mid-stage: it is manifested as increased serous nasal fluid and serous ocular secretions, and decreased appetite; late stage: it is manifested as purulent nasal fluid, dry or even cracked nose, mucous secretions on the corners of the mouth, highly depressed spirit, reduced or even annulled appetite, but eager to drink, the body temperature of 39.5° C.~41.5° C., accelerated breathing, rough breathing sounds, often accompanied by heart rate irregularities, and even vomiting and diarrhea. The vomit is mucus or yellow liquid, while the stool is dark brown or covered with mucus. As the progress of the disease course, dogs with canine distemper often develop secondary bacterial infections due to their decreased resistance.

4. Dosage and Mode of Administration

Anemoside B4 injection was intravenously injected, 2 mL/time in low-dose group, 4 mL/time in medium-dose group, 8 mL/time in high-dose group, once a day; anemoside B4 injection was intramuscularly injected, 1 mL/time in low-dose group, 2 mL/time in the middle-dose group, 4 mL/time in the high-dose group, twice a day; the treatment was kept for 14 days.

5. Experimental Results

TABLE 14

The research results of anemoside B4 for treatment of canine distemper ($\bar{x} \pm SD$, n = 10)

| Groups | Numbers treated (dog) | Cure (dog) | Death (dog) |
|---|---|---|---|
| Blank control group | 10 | 1 | 9 |
| Low-dose group of intramuscular injection | 10 | 3 | 7 |
| Medium-dose group of intramuscular injection | 10 | 4 | 6 |
| High-dose group of intramuscular injection | 10 | 5 | 5 |
| Low-dose group of intravenus injection | 10 | 4 | 6 |
| Medium-dose group of intravenus injection | 10 | 5 | 5 |
| High-dose group of intravenus injection | 10 | 6 | 4 |

According to the experimental results, anemoside B4 showed a better therapeutic effect on canine distemper.

Experimental Example 6

Canine Renal Failure

1. Test Drug

Anemoside B4 injection prepared in example 3, with a concentration of 50 mg/mL.

2. Test Animals

Dogs suffering from canine distemper are cases received by various pet hospitals in Chengdu city.

3. Symptoms of Sick Dogs

The sick dog has poor appetite, depression, lethargy, vomiting repeatedly, fetid mouth odor, decreased body temperature, and been vaccinated with a negative CPV test. Blood biochemical tests for urea, creatinine, and inorganic phosphorus are 2 times more than the normal value, and the biochemical indicators of other organs were normal, and the abdominal B-ultrasonic examination of the sick dog showed changes in the size and shape of the kidney.

4. Dosage and Mode of Administration

Anemoside B4 injection was intravenously injected, 2 mL/time in low-dose group, 4 mL/time in medium-dose group, 8 mL/time in high-dose group, once a day; anemoside B4 injection was intramuscularly injected, 1 mL/time in low-dose group, 2 mL/time in the middle-dose group, 4 mL/time in the high-dose group, twice a day; the treatment was kept for 14 days.

5. Experimental Results

TABLE 15

The research results of anemoside B4 for treatment of canine renal failure ($\bar{x} \pm SD$, n = 10)

| Groups | Numbers treated (dog) | Body temperature (° C.) | Urea (mmol/L) | Creatinine (μmol/L) | Inorganic phosphous (mmol/L) | Mortality rate (%) |
|---|---|---|---|---|---|---|
| Blank control group | 10 | 37.1 ± 0.4 | 35.0 ± 0.6 | 412 ± 41 | 9.1 ± 0.8 | 80 |
| Low-dose group of intramuscular injection | 10 | 37.8 ± 0.3 | 20.8 ± 0.5 | 130 ± 19* | 1.6 ± 0.02* | 60 |
| Medium-dose group of intramuscular injection | 10 | 38.2 ± 0.4 | 17.5 ± 0.7* | 120 ± 26* | 2.0 ± 0.03* | 50 |
| High-dose group of intramuscular injection | 10 | 38.5 ± 0.2 | 14.2 ± 0.4* | 100 ± 30* | 1.4 ± 0.08* | 40 |
| Low-dose group of intravenus injection | 10 | 38.3 ± 0.5* | 11.8 ± 0.6* | 117 ± 25* | 1.1 ± 0.05* | 40 |
| Medium-dose group of intravenus injection | 10 | 38.5 ± 0.3* | 9.9 ± 0.8* | 115 ± 12* | 1.5 ± 0.04* | 30 |

TABLE 15-continued

The research results of anemoside B4 for treatment of canine renal failure ($\bar{x} \pm SD$, n = 10)

| Groups | Numbers treated (dog) | Body temperature (° C.) | Urea (mmol/L) | Creatinine (μmol/L) | Inorganic phosphous (mmol/L) | Mortality rate (%) |
|---|---|---|---|---|---|---|
| High-dose group of intravenus injection | 10 | 38.6 ± 0.4* | 8.7 ± 0.3* | 109 ± 20* | 0.9 ± 0.06* | 20 |

Note:
*denotes the obvious difference compared with the blank control group, $p < 0.05$.
According to the experimental results, anemoside B4 showed a certain therapeutic effect on canine renal failure, and as the increase of the therapeutic dose, the mortality of sick dogs presented a decreasing trend.

Experimental Example 7

Canine Acute Nephritis

1. Test Drug

Anemoside B4 injection prepared in example 3, with a concentration of 50 mg/mL.

2. Test Animals

Dogs suffering from acute nephritis are cases received by various pet hospitals in Chengdu city.

3. Symptoms of Sick Dogs

The sick dogs are characterized by loss of appetite, indigestion, depression, and a slight increase in body temperature. On palpation of the kidney area, the dog felt pain, and the frequency of urination increased significantly, but the urine output was small, showing a small amount but multiple times, moreover, dark red hematuria appeared. Urine examination showed positive protein. Microscopic examination of urine sediment showed white blood cells, red blood cells and a large number of renal epithelial cells.

4. Dosage and Mode of Administration

Anemoside B4 injection was intravenously injected, 2 mL/time in low-dose group, 4 mL/time in medium-dose group, 8 mL/time in high-dose group, once a day; anemoside B4 injection was intramuscularly injected, 1 mL/time in low-dose group, 2 mL/time in the middle-dose group, 4 mL/time in the high-dose group, twice a day; the treatment was kept for 14 days.

5. Experimental Results

TABLE 16

The research results of anemoside B4 for treatment of canine acute nephritis ($\bar{x} \pm SD$, n = 10)

| Groups | Numbers of treatment (dog) | Body temperature (° C.) | Positive rate of urine protein (+++, %) | Urine specific gravity | Positive rate of white blood cell (+++, %) | Mortality rate (%) |
|---|---|---|---|---|---|---|
| Blank control group | 10 | 39.7 ± 0.3 | 100 | 1.220 ± 0.63 | 100 | 80 |
| Low-dose group of intramuscular injection | 10 | 39.5 ± 0.3 | 80 | 1.123 ± 0.01 | 80 | 60 |
| Medium-dose group of intramuscular injection | 10 | 39.3 ± 0.4 | 70 | 1.094 ± 0.04* | 80 | 60 |
| High-dose group of intramuscular injection | 10 | 39.0 ± 0.2* | 60 | 1.064 ± 0.02* | 70 | 50 |
| Low-dose group of intravenus injection | 10 | 38.7 ± 0.5 | 50 | 1.017 ± 0.25 | 60 | 50 |
| Medium-dose group of intravenus injection | 10 | 38.8 ± 0.3* | 40 | 1.005 ± 0.09* | 40 | 40 |
| High-dose group of intravenus injection | 10 | 38.5 ± 0.4* | 30 | 1.003 ± 0.01* | 30 | 30 |

Note:
*denotes the obvious difference compared with the blank control group, $p < 0.05$.
According to the experimental results, anemoside B4 showed a certain therapeutic effect on canine acute nephritis, and as the increase of the therapeutic dose, the mortality of sick dogs presented a decreasing trend.

In summary, anemoside B4 of the present invention has stronger biological activity, and has excellent therapeutic effects on endometritis, foot rot disease, feline parvovirus, canine parvovirus, canine distemper, canine renal failure, and canine acute nephritis.

The invention claimed is:

1. A method of treating cow endometritis or cow foot rot disease, comprising administering an effective amount of a composition to a subject in need thereof, wherein the composition consists of compound anemoside B4 of formula I or pharmaceutically acceptable salts thereof:

Formula I

2. The method according to claim 1, wherein the composition is administered by intramuscular, intrauterine, or intravenus injection when treating cow endometritis.

3. The method according to claim 1, wherein the composition is administered by subcutaneous injection, intravenus injection, or pulvis when treating cow foot rot disease.

4. A method of treating canine parvovirus disease or feline parvovirus disease, comprising administering an effective amount of a composition to a subject in need thereof, wherein the composition consists of compound anemoside B4 of formula I or pharmaceutically acceptable salts thereof.

5. A method of treating canine distemper, canine renal failure, or canine acute nephritis, comprising administering an effective amount of a composition to a subject in need thereof, wherein the composition consists of compound anemoside B4 of formula I or pharmaceutically acceptable salts thereof.

* * * * *